(12) United States Patent
Ogawa et al.

(10) Patent No.: US 7,083,992 B2
(45) Date of Patent: Aug. 1, 2006

(54) METHOD OF OBSERVATION BY TRANSMISSION ELECTRON MICROSCOPY

(75) Inventors: Shinichi Ogawa, Osaka (JP); Yasuhide Inoue, Kanagawa (JP); Junichi Shimanuki, Kanagawa (JP); Hirotaro Mori, Osaka (JP)

(73) Assignee: Matsushita Electric Industrial Co., Ltd., Kadoma (JP)

( * ) Notice: Subject to any disclaimer, the term of this patent is extended or adjusted under 35 U.S.C. 154(b) by 0 days.

(21) Appl. No.: 10/944,842

(22) Filed: Sep. 21, 2004

(65) Prior Publication Data

US 2005/0042781 A1    Feb. 24, 2005

(51) Int. Cl.
 *G01L 21/66*    (2006.01)
(52) U.S. Cl. ....................................................... 438/16
(58) Field of Classification Search .................. 438/5, 438/7, 10, 14–18, 22, 34–36, 29, 31, 128–130, 438/149, 484, 538
See application file for complete search history.

(56) References Cited

U.S. PATENT DOCUMENTS

| | | | |
|---|---|---|---|
| 5,788,853 A | | 8/1998 | Zenhausern |
| 5,866,905 A | * | 2/1999 | Kakibayashi et al. ........ 250/311 |
| 5,986,285 A | * | 11/1999 | Yagi ............................. 257/53 |
| 6,448,556 B1 | * | 9/2002 | Cowley et al. .............. 250/311 |

FOREIGN PATENT DOCUMENTS

| | | |
|---|---|---|
| JP | 2003-14661 | 1/2003 |
| JP | 2004-111839 | 4/2004 |

OTHER PUBLICATIONS

Nigel D. Browning and Stephen Pennycook, "Characterization of High Tc Materials and Devies by Eectron Microscopy", Cambridge University Press. pp. 1-21.*

Shinichi Ogawa, et al., "3-Dimentional TEM Stereo Observation Technology for Characterization of Pores in Low-k Film", International Interconnect Technology Conference, Jun. 2003, 3 pages.

J. Shimanuki, et al., "3-Dimentional evaluation of pores in a low-k film TEM stereoscopic observation method", Preprint of annual meeting of Japan Society of Applied Physics, Mar. 2002, 1 page.

(Continued)

*Primary Examiner*—Michael Lebentritt
*Assistant Examiner*—Andre' Stevenson
(74) *Attorney, Agent, or Firm*—Oblon, Spivak, McClelland, Maier & Neustadt, P.C.

(57) ABSTRACT

A method for observing defects in an amorphous material by transmission electron microscopy. The method generates an incident electron beam into the amorphous material, eliminates a generated diffraction wave to form an image only by a transmission wave coming through the amorphous material, and observes the image under an under-focus condition.

14 Claims, 13 Drawing Sheets

OTHER PUBLICATIONS

J. Shimanuki, et al., "Behavior of pores in a thin low-k film during anneal—ex-situ TEM observation method", Preprint of annual meeting of Japan Society of Applied Physics, Sep. 2002, 1 page.

J. Shimanuki, et al., "3-Dimentional evaluation of pores in a porous silica film using TEM stereoscopic observation method", Preprint of the Japanese Society of Microscopy, Jun. 2003, 1 page.

* cited by examiner

METHOD OF OBSERVATION BY TRANSMISSION ELECTRON MICROSCOPY

BACKGROUND OF THE INVENTION

1. Field of the Invention

The present invention relates to a method of observation by the transmission electron microscopy, and particularly to an observation method by the transmission electron microscopy capable of clearly observing the distribution condition of defects such as pores in an amorphous material.

1. Discussion of the Background

Through the process of development of various materials and of devices, grasping the distribution condition of defects in an amorphous material is a critical issue. In the development of semiconductor integrated circuit devices, for example, the interconnection rule has entered a generation of 100 nanometer level, thus the higher integration requires a multilayer interconnection structure applying an interconnection layer made of copper and an interlayer insulating layer made of an insulating material.

In a semiconductor device having that type of multilayer interconnection structure, the dielectric constant of the insulating material structuring the interlayer insulating film is required to be decreased to reduce the parasitic capacitance between interconnections. An effective method to reduce the dielectric constant of insulating materials such as $SiO_x$ is to form a porous (low-k) material by introducing pores therein.

However, in the case that the semiconductor integrated circuit is formed using a porous insulating material, the three-dimensional shape and the distribution of pores give significant influence on the mechanical and electrical characteristics of the interlayer insulating film. For instance, when pores penetrate the insulating film to create continued pores, they form what is called the "leak path", which induces leak current and degradation in withstand voltage of the device element.

Accordingly, it is very critical to grasp the three-dimensional shape and the distribution of pores in the development of a Cu/low-k multilayer interconnection structure. There are reports on the method for evaluating the pore size, (for example, W. L. Wu et al., J. Appl. Phys., 87 p1193 (2000))

The method disclosed by W. L. Wu et al. (J. Appl. Phys., 87 p1193 (2000)), however, gives only a speculation of the three-dimensional shape and the distribution of pores through calculations based on various assumptions, and leaves unknown conditions of actual shape and distribution of pores.

In addition, for the case of multilayer interconnection structure of a semiconductor integrated circuit, for example, the interlayer insulating film is made of an amorphous material, while the metallic sections such as the interconnection layer and the copper structuring the buried plug are in a polycrystalline state. Accordingly, observation of defects or the like in the metallic sections often becomes inadequate under the same observation condition with that for the amorphous insulating layer.

To this point, the inventors of the present invention published a result of observation on the shape and the distribution of pores existing in an amorphous material applying a stereoscopic observation method by the transmission electron microscopy (Proceedings of the 49th Joint Meeting on Applied Physics, spring 2002, No. 2, p853 29p-F-3).

SUMMARY OF THE INVENTION

The present invention has been accomplished based on the contents of the disclosure of the Proceedings of the 49th Joint Meeting on Applied Physics, spring 2002, No. 2, pp53 29p-F-3, and an object of the present invention is to provide an observation method by the transmission electron microscopy capable of clearly observing the distribution of defects such as pores in an amorphous material.

According to an aspect of the invention, there is provided a method for observing defect in an amorphous material by transmission electron microscopy, comprising the steps of: incident electron beam into the amorphous material; eliminating a generated diffraction wave to form an image only by a transmission wave coming through the amorphous material; and observing the image under an under-focus condition.

According to another aspect of the invention, there is provided a method for respectively observing an amorphous material and a crystalline material in a composite material containing both of the amorphous material and the crystalline material by transmission electron microscopy, wherein, when observing a defect in the amorphous material, electron beam is injected into the amorphous material, and a generated diffraction wave is eliminated, then an image is formed only by a transmission wave coming through the amorphous material to conduct observation thereof under an under-focus condition, while when observing the crystalline material, electron beam is injected into the crystalline material, and an image is formed by a generated diffraction wave and by a transmission wave coming through the crystalline material to conduct observation thereof.

The term "amorphous material" referred to the present application specification signifies a material in a state of what is called the completely disordered non-crystalline state, and further includes a fine crystal grain such as small-crystal, micro-crystal, and nano-crystal, and a material having short range ordered structure and the like.

The term "crystalline material" referred to the present application specification signifies both a material in a polycrystalline state and a material in a single-crystalline state.

BRIEF DESCRIPTION OF THE DRAWINGS

The present invention will be understood more fully from the detailed description given herebelow and from the accompanying drawings of the embodiments of the invention. However, the drawings are not intended to imply limitation of the invention to a specific embodiment, but are for explanation and understanding only.

In the drawings.

DETAILED DESCRIPTION

Figure 1:
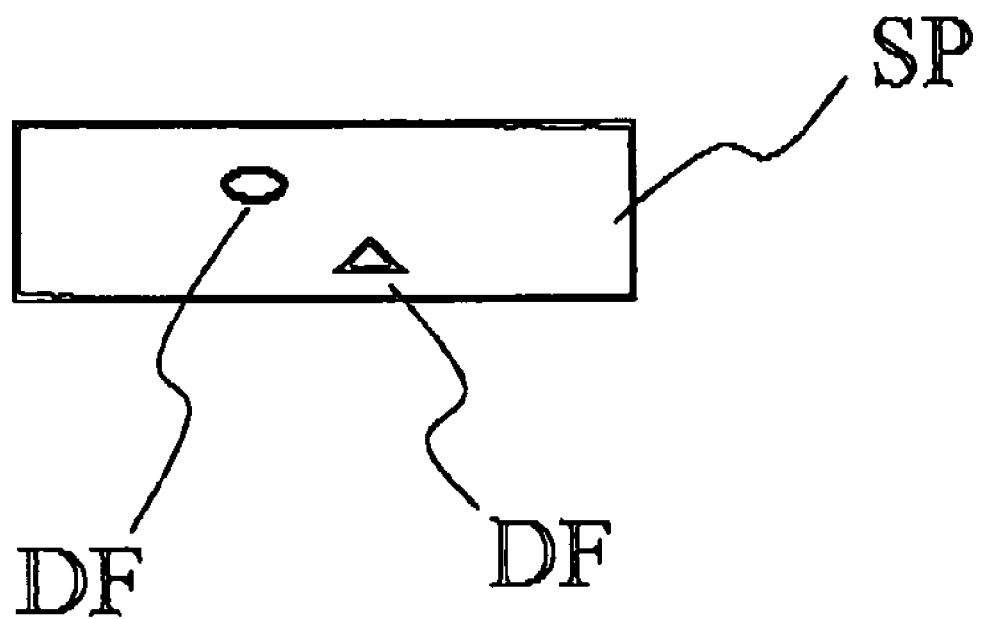
FIG. 1 is a typical view of an example of specimen capable of being observed in the embodiment of the invention.

An embodiment of the present invention will be described below referring to the drawings.

According to the embodiment of the invention, the observation of defects such as pores distributed inside an interlayer insulating film in a semiconductor device which is typically shown in FIG. 12 (given later) is conducted by the stereoscopic observation of the transmission electron microscopy (TEM) under an under-focus condition, utilizing only the transmission wave while eliminating the diffraction wave.

FIG. 1 typically shows a drawing of an example of a specimen capable of being observed according to the embodiment of the invention. That is, the figure shows an amorphous specimen SP (material being observed) such as $SiO_x$ containing defects DF such as pores. The size of the defect DF is in an approximate range from several nanometers to several tens of nanometers. The thickness of the specimen SP is required to be thin to allow the electron beam to transmit therethrough in the transmission electron microscopy. For example, with a transmission electron microscope giving 200 kV of acceleration voltage, the thickness of the specimen SP is selected to be smaller than about 200 nm.

According to the embodiment of the invention, clear observation of the shape and the distribution of defects such as pores DF existing in that type of amorphous material becomes available.

The following is a more detailed description of the conditions of the embodiment of the invention.

Figure 2:
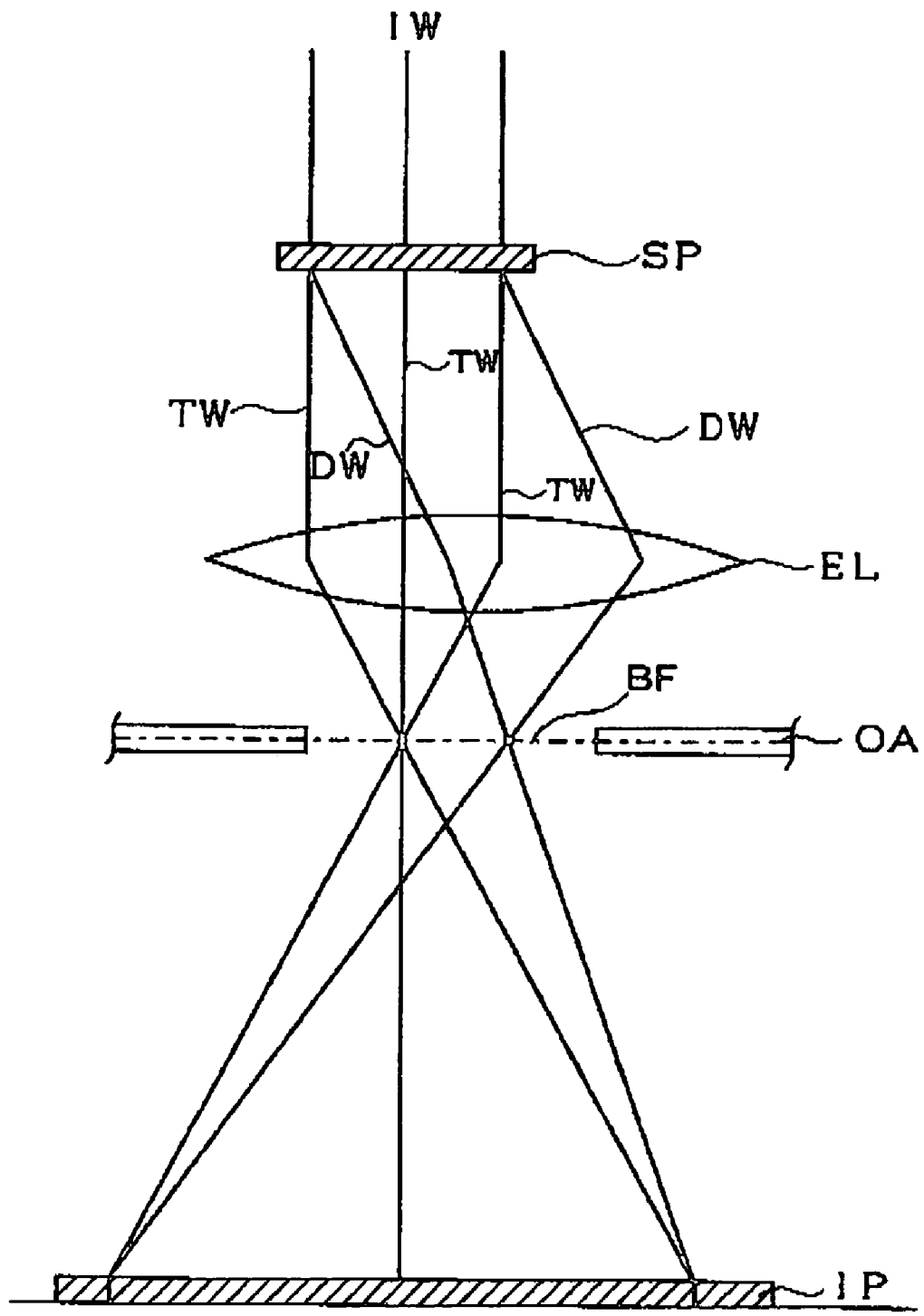
FIG. 2 is a typical view illustrating the image-formation mechanism by the transmission electron microscopy.

FIG. 2 shows a typical drawing for illustrating the image-formation mechanism by the transmission electron microscopy.

When observing the structure of thin film specimen SP by the transmission electron microscopy, parallel incident electron beam IW is applied to the specimen SP. The electron beam coming through the specimen SP is divided into the electron beam (transmission wave) TW which permeated straight through the specimen SP without suffering interaction with the specimen SP therebetween, and a large number of electron beams (diffraction waves) DW of which their direction is changed resulting from scattering on various atomic planes in the specimen SP.

Each transmission wave TW and diffraction wave DW converges on a back focal plane BF by the focusing effect of an electromagnetic lens EL. The obtained TEM image differs with the selection of electron beam (waves) of either the transmission wave TW, which is converged on the back focal plane BF, or the plurality of diffraction waves DW, using an objective diaphragm OA.

In the case of normal TEM observations, the transmission wave TW and the diffraction wave (single wave or plural waves) DW enter the objective diaphragm OA to form an image. In that case, the transmission wave TW and the diffraction wave DW interfere with each other to generate an interference fringe, which fringe then forms an image on an imaging plane IP. The interference fringe corresponds to the distance between the atomic planes, which generates the diffraction waves DW, thus the microstructure reflecting the information of atomic plane is obtained as a TEM image.

To the contrary, when the image is formed only by the transmission wave TW based on the embodiment of the invention, no microstructure corresponding to the atomic plane is obtained because of the absence of interference with the diffraction wave DW. In other words, there is appeared a tendency of rejecting periodic information in the structure of the specimen SP. In that case, the information provided from the TEM image is a portion, which deviates from the averaged structure of the specimen SP, for example the contour of a pore or the domain different from surrounding area in terms of density. Thus a macroscopic structure, compared with the microstructure on the atomic plane, is observed.

Figure 3A:
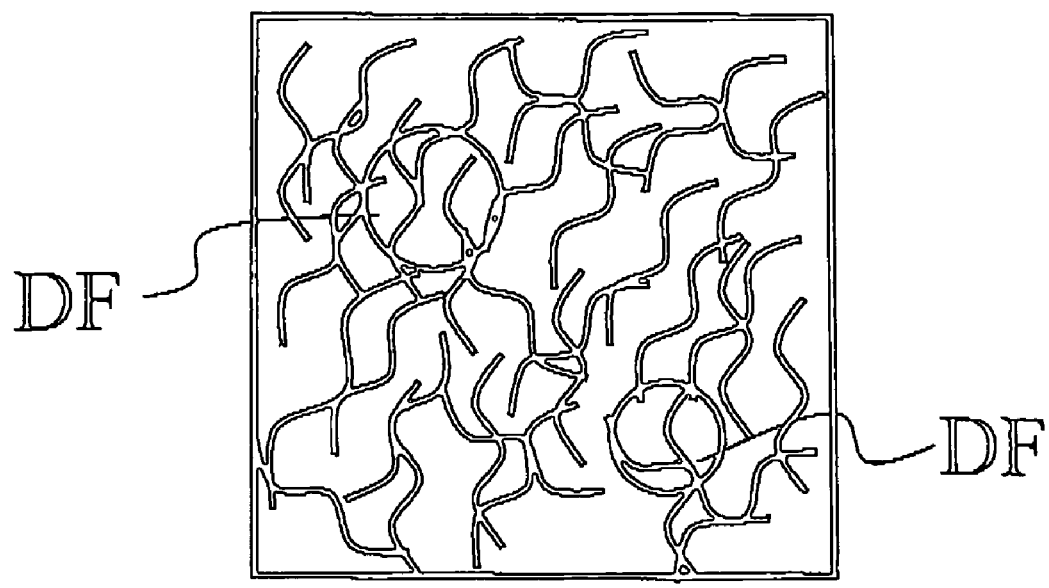
FIG. 3 is a conceptual view illustrating the effect of elimination of diffraction wave under the observation of an amorphous specimen.
Figure 3B:
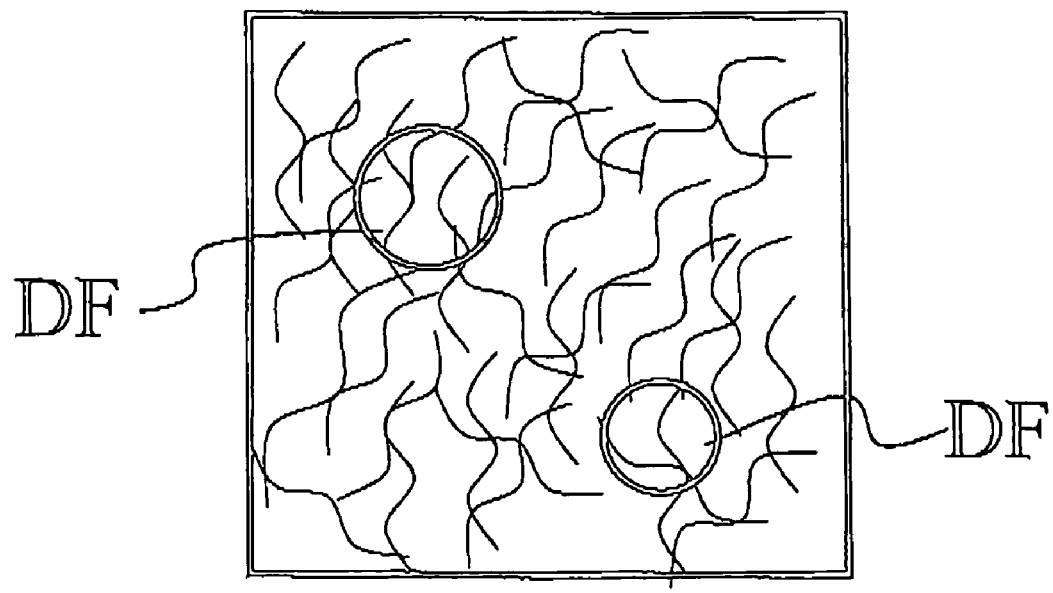

FIGS. 3A, and 3B show conceptual drawings for illustrating the effect of elimination of diffraction wave under the observation of an amorphous specimen. That is, these drawings show the TEM images of pores DF in an amorphous material given by the transmission electron microscopy. FIG. 3A shows a TEM image formed using both the transmission wave TW and the diffraction wave DW, and FIG. 3B shows a TEM image formed only by the transmission wave TW.

When an image is formed using both the transmission wave TW and the diffraction wave DW, the phase contrast in the obtained TEM image becomes intense, as shown in FIG. 3A, thus the contrast of the defect DF becomes relatively difficult to obtain. The phase contrast is presumably a contrast, which is generated by the interference between the transmission wave TW and the diffraction wave DW responding to the microstructure, at sub-nanometer order, in the amorphous material. That is, when the image is formed using the diffraction wave DW, the phase contrast corresponding to the microstructure of the amorphous material becomes intense, and the contrast of defect DF becomes relatively weak.

On the other hand, when the image is formed only by the transmission wave TW, the phase contrast becomes weak, as shown in FIG. 3B, and the contrast of defect DF becomes relatively intense. The phenomenon presumably arises because the interference with the diffraction wave DF does not occur and the phase contrast corresponding to the microstructure of the amorphous material is suppressed in the TEM image.

As described above, when the defect DF such as pore existing in an amorphous material is observed, it is important to form an image using only the transmission wave, different from the normal TEM observations.

The focus effect is described below. When observing clearly a defect in an amorphous material, the focus condition is also important for the TEM observation.

Figure 4:
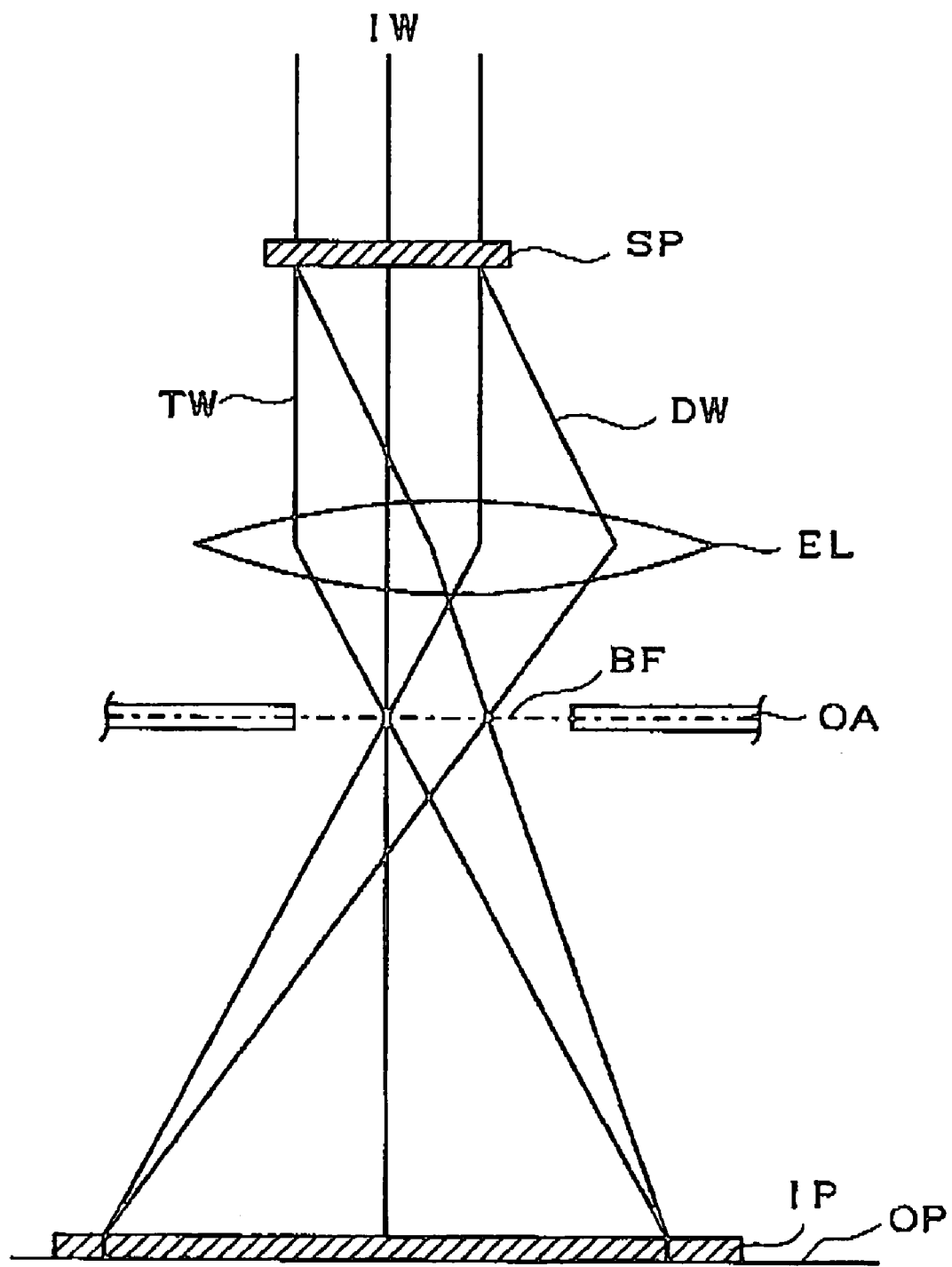
FIG. 4 is a typical view of an example of "just-in-focus" state in the transmission electron microscopy.

FIG. 4 shows a typical drawing of an example of "just-in-focus" state for the transmission electron microscopy. Namely, under the just-in-focus condition, the imaging plane IP for the focusing effect of the electromagnetic lens EL and the observation plane OP coincide with each other, Generally, the focus condition to obtain the microstructure of atomic plane is narrow. Since the TEN observation allows most of the electron beam IW to pass through the specimen SP without being absorbed therein, the just-in-focus state, which makes the observation plane coincide with the imaging plane, as shown in FIG. 4, gives very little contrast on the observation image, which results in difficulty in clear observation.

Figure 5:
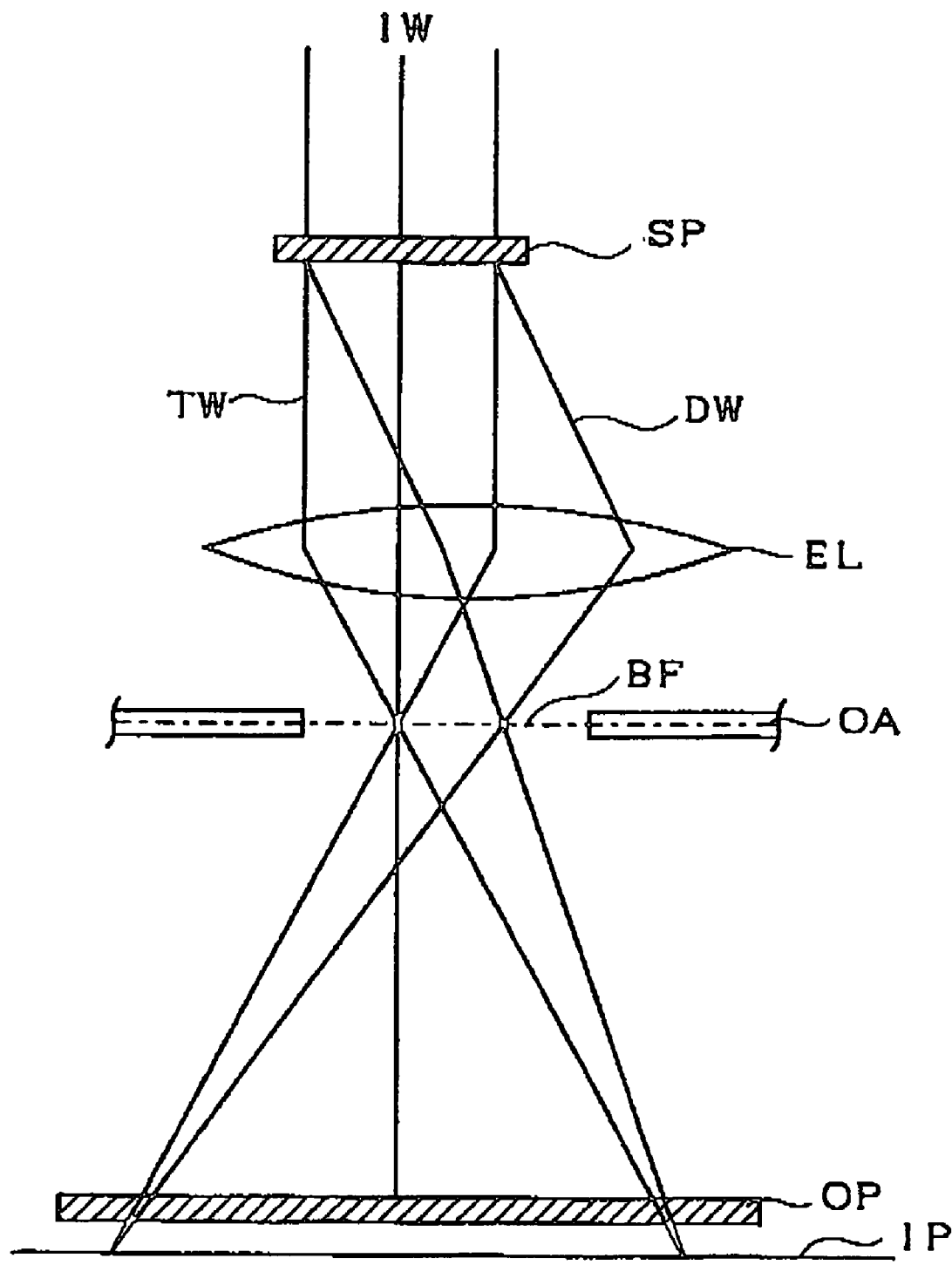
FIG. 5 shows a typical view of an example of "Scherzer focus (optimum focus)" in the transmission electron microscopy.

FIG. 5 shows a typical drawing of an example of "Scherzer focus (optimum focus)" in the transmission electron microscopy. That is, under the Scherzer focus condition, the focus is given to bring the imaging plane IP to slightly below the observation plane OP.

As seen in normal TEM observations, when the microstructure of atomic plane is observed while making the transmission wave and the diffraction wave interfere with each other, the Scherzer focus provides the contrast of the observed image in a 1 to 1 relation corresponding to the position of individual atoms in the specimen, which allows the clearest observation. If the condition becomes outside the Scherzer focus condition, the observation image OP becomes out-focus to fail in clear observation of microstructure.

To the contrary, when the observation of defect in an amorphous material is given based on the embodiment of the invention, it is preferable to conduct the observation under a condition that the focus condition is shifted to further under-focus side.

Figure 6:
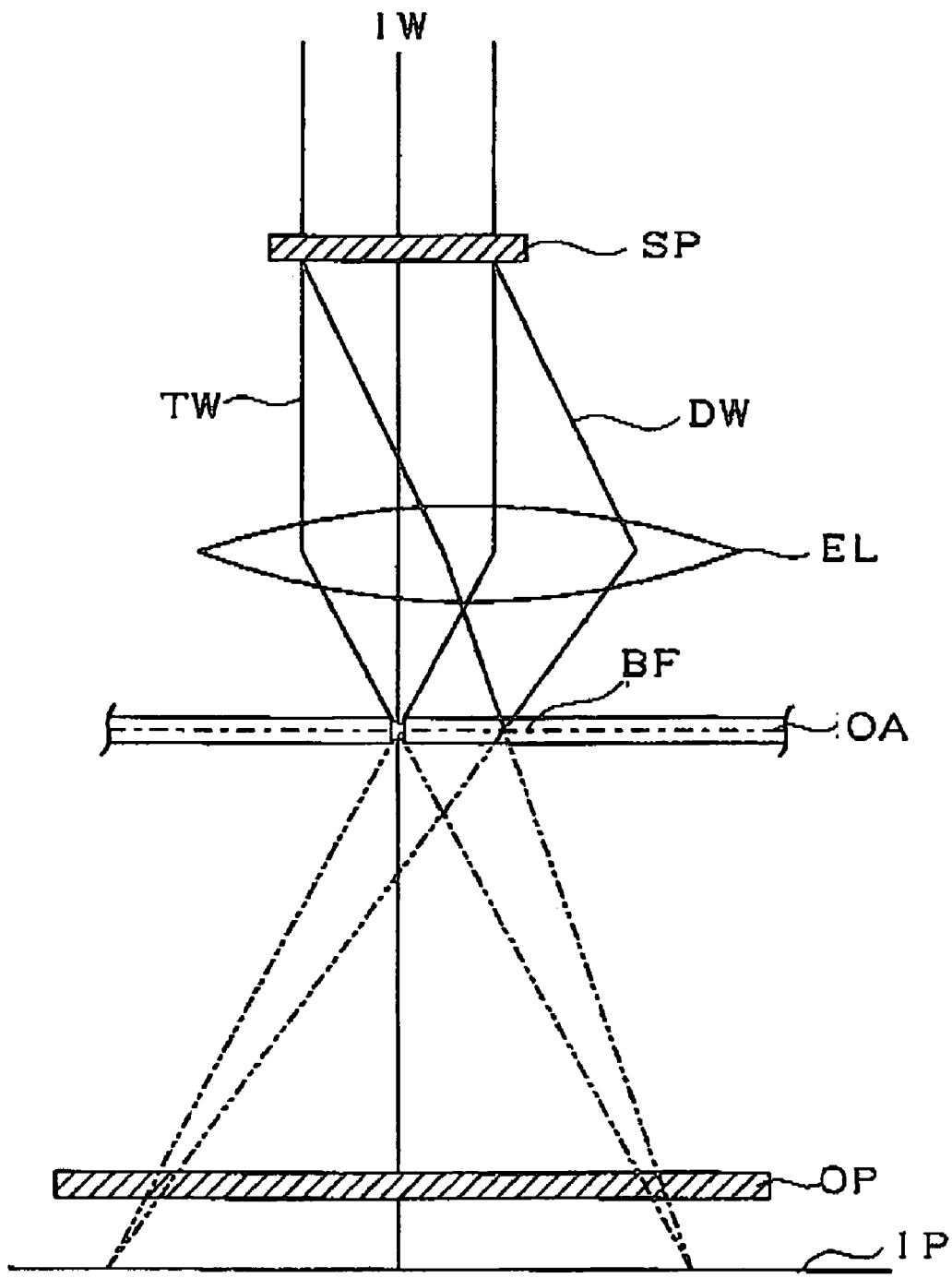
FIG. 6 is a typical view of an example of observation condition based on the embodiment of the invention.

FIG. 6 shows a typical drawing illustrating an example of observation condition based on the embodiment of the invention. The target defect in the amorphous material has a macroscopic structure compared with the microstructure of the atomic plane. Accordingly, as described above, by forming an image only by the transmission wave TW, and simultaneously by selecting the focus condition to further "under-focus" side than the Scherzer focus condition, the phase contrast originated from the microstructure of the amorphous material is weakened, and the contrast on the macroscopic defect is obtained relatively intensely.

Figure 7A:
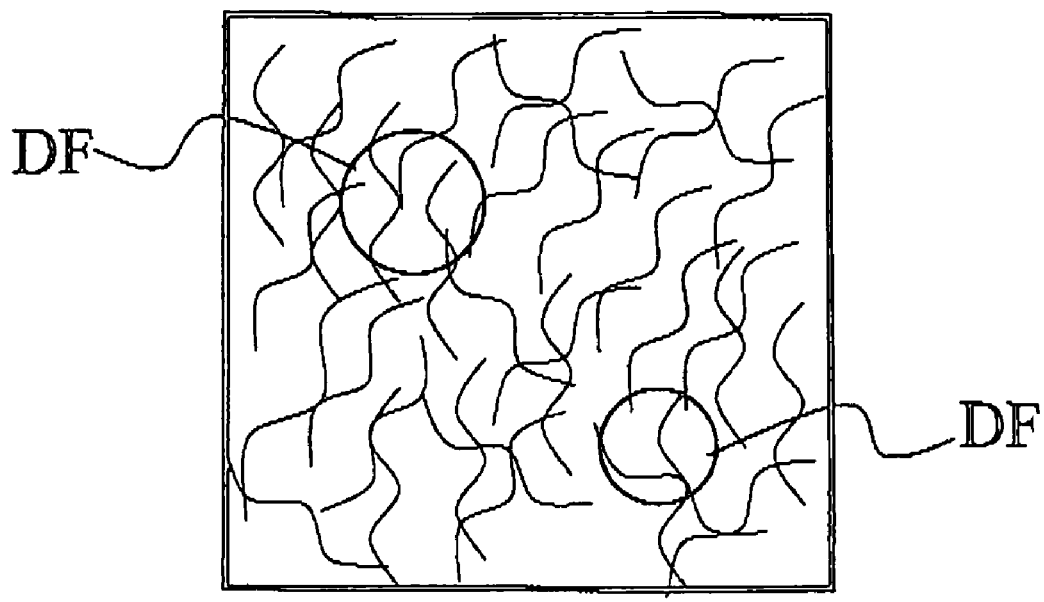
FIG. 7 is a typical view illustrating TEM images observed for identifying the defects in amorphous material under the respective focus conditions.
Figure 7B:
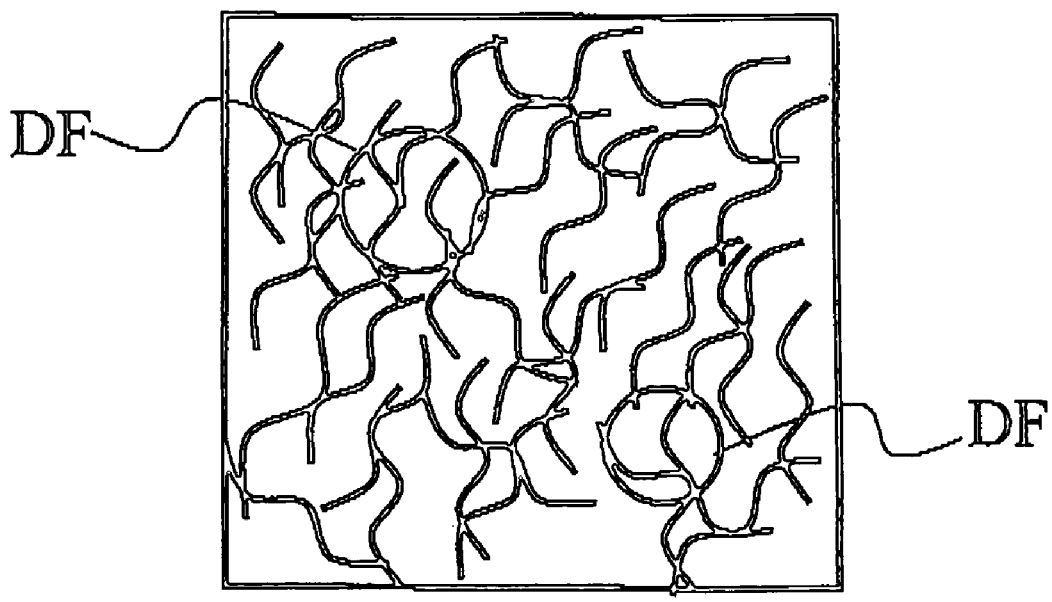
Figure 7C:
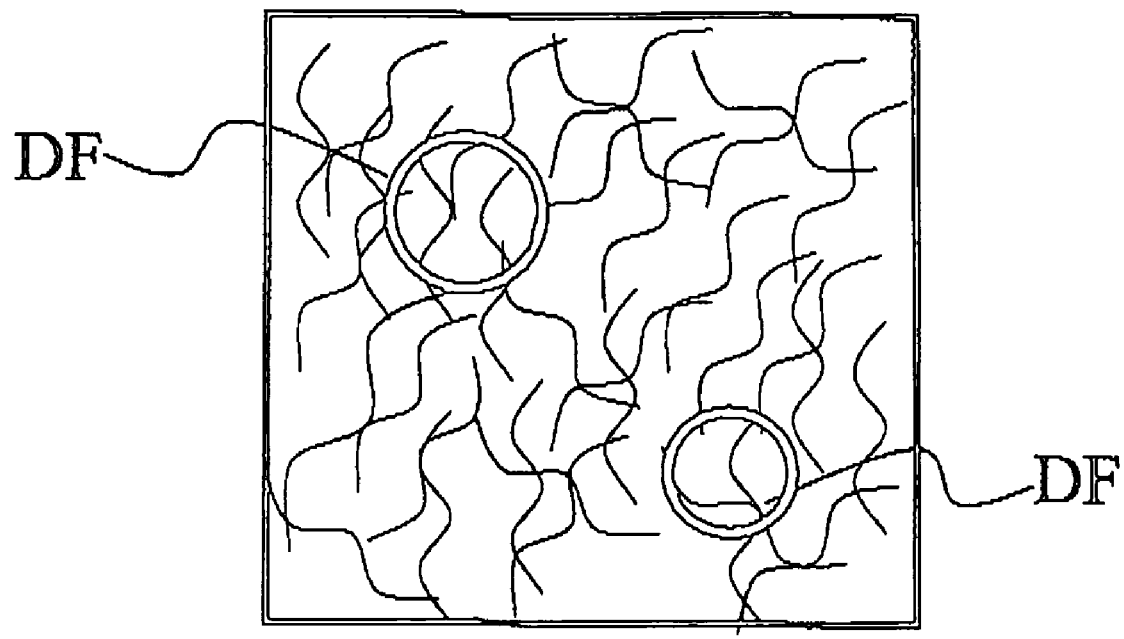

FIGS. 7A to 7C show typical drawings of observed TEM images of defect in an amorphous material observed under the respective focus conditions.

That is, when the observation is given under the just-in-focus condition, the phase contrast originated from the microstructure of the amorphous material becomes weak, as shown in FIG. 7A. The contrast of defect DF also becomes weak, thus the clear observation becomes difficult to attain.

For the case of Scherzer focus condition, which is a normal observation condition of TEM, the contrast of defect DF becomes intense, as shown in FIG. 7B. The phase contrast originated from the microstructure of the amorphous material also becomes intense, and the observation of the defect DF also becomes difficult.

To the contrary, when the observation is given by forming an image only by the transmission wave and under an under-focus condition, the phase contrast originated from the microstructure of the amorphous material becomes weak, as shown in FIG. 7C, and the observation of the pore DF becomes easy because the contour of the pore is emphasized, though the contour is somewhat out-focus owing to the under-focus condition.

As described above, there has been no clear observation of pore in amorphous material by the transmission electron microscopy until now because the normal TEM observation is carried out by introducing both the transmission wave and the diffraction wave into the objective diaphragm to observe the microstructure of the specimen. In addition, the observation has been given under the Scherzer focus condition as the focus condition to allow observing a microstructure, which shows the atomic arrangement.

Under the observation condition, however, the phase contrast corresponding to the microstructure of sub-nanometer order of the amorphous material becomes intense so that the contrast of pore having larger size, or several nanometers, is screened behind the phase contrast to fail in clear identification.

To the contrary, according to the embodiment of the invention, the observation is given by forming an image only by the transmission wave and under an under-focus condition, thus the phase contrast of the amorphous material is weakened to provide a strong contrast of the defect.

Furthermore, according to the embodiment of the invention, the stereoscopic observation is applied to generate further clear contrast of the defects in an amorphous material, and to grasp the three-dimensional shape and the distribution of the defects.

Figure 8:
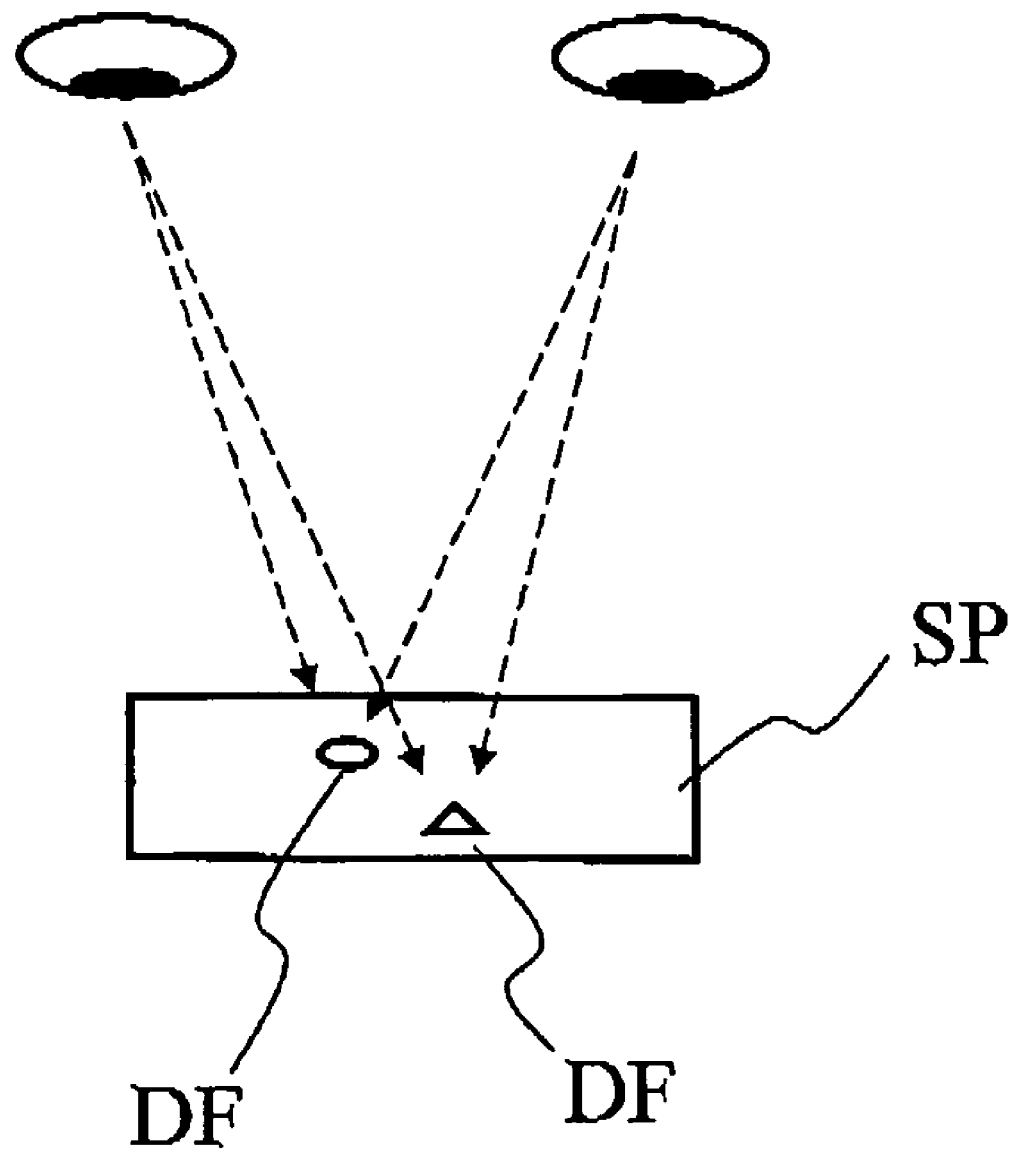
FIG. 8 is a typical view illustrating the principle of the stereoscopic observation.

FIG. 8 is a typical drawing illustrating the principle of the stereoscopic observation. When defects DF exist in the specimen SP, observation of the defects is given from different viewpoints (for example, right eye and left eye) to grasp the three-dimensional shape and the distribution of the defects.

Figure 9A:
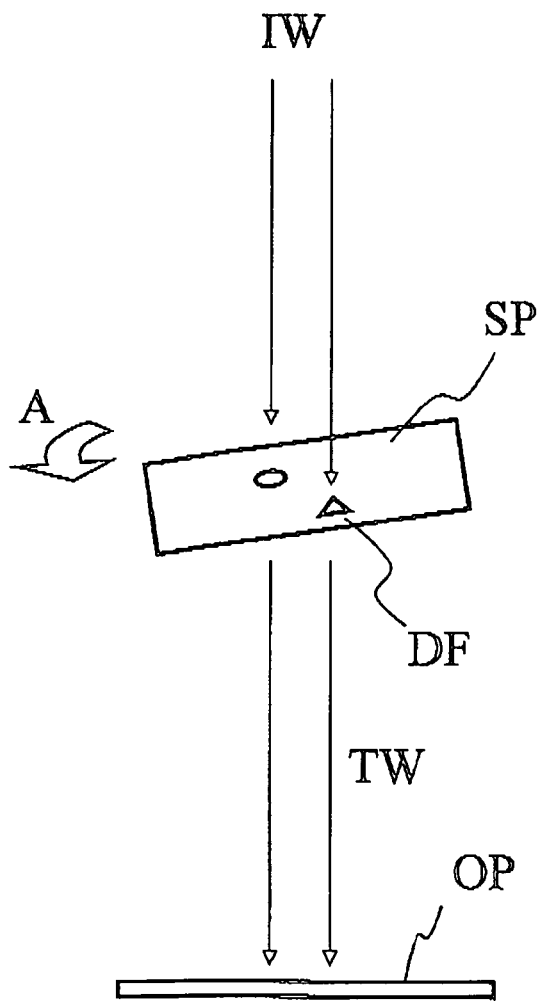
FIG. 9 is a typical view illustrating the method of stereoscopic observation by the transmission electron microscopy based on the embodiment of the invention.
Figure 9B:
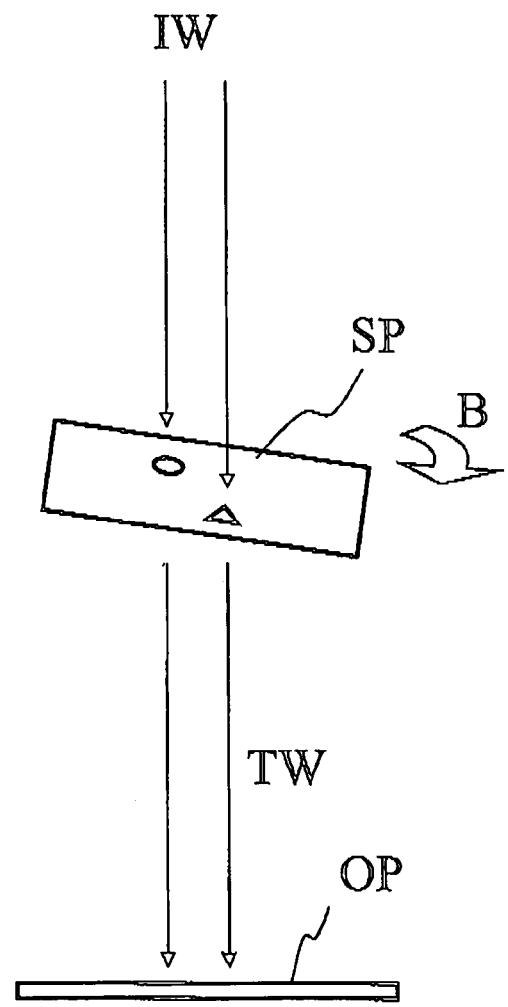

FIGS. 9A, and 9B are typical drawings illustrating the method of stereoscopic observation by the transmission electron microscopy according to the embodiment of the invention.

The transmission electron microscopy allows stereoscopic observation by tilting the specimen SP to form TEM images at the respective different angles.

That is, as shown in FIG. 9A, the specimen SP is tilted in the arrow A direction to form a TEM image using the transmission wave TW under an under-focus condition.

Then, as shown in FIG. 9B, the specimen SP is tilted in the arrow B direction, opposite to the arrow A direction, to form a TEM image using the transmission wave TW under an under-focus condition.

Once those TEM images are formed under the stereoscopic observation, three-dimensional information is available by adequately composing these TEM images.

Figure 10:
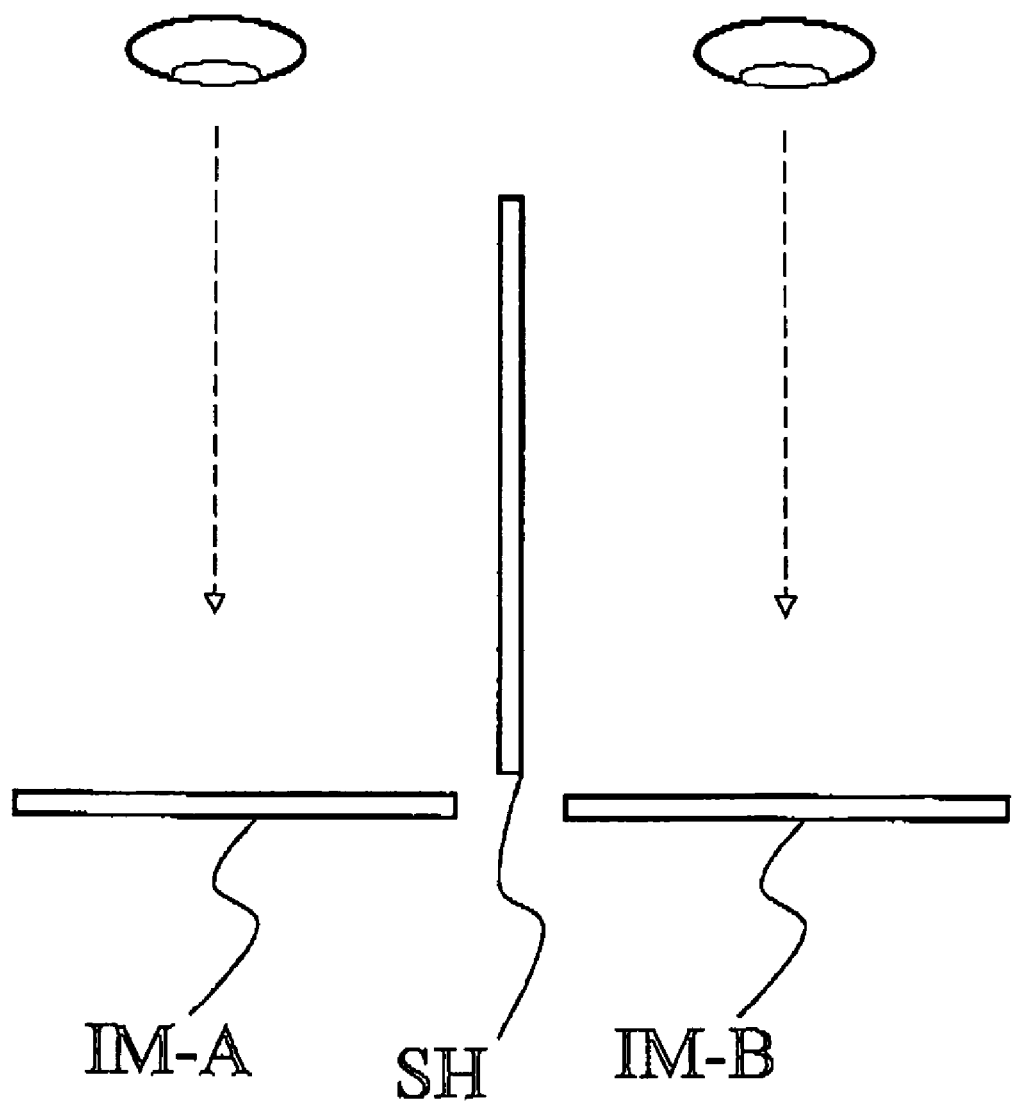
FIG. 10 is a typical view illustrating the principle for composing a pair of stereo-images.

FIG. 10 is a typical drawing illustrating the principle for composing a pair of stereoscopic images. When a pair of stereoscopic TEM images, IM-A and IM-B, is formed using a method such as the one exampled in FIGS. 9A, 9B, these TEM images are screened by a shield SH, and then are observed by the right eye and the left eye, respectively, thus composing these images to form a three-dimensional image. As a result, the defects DF in the amorphous material are grasped in terms of three-dimensional shape and distribution.

Furthermore, the composing of that type of a pair of stereoscopic TEM images provides an effect of weakening the background noise by averaging thereof. That is, as shown in FIG. 3 and FIG. 7, TEM observation of an amorphous material gives a phase contrast corresponding to the microstructure. To the contrary, composing of a pair of stereoscopic TEM images cancels the phase contrast on the respective stereo-TEM images to relatively weaken the phase contrast. On the other hand, there is obtained the effect that the contrast of defect DF is emphasized to allow clearer observation.

Figure 11:
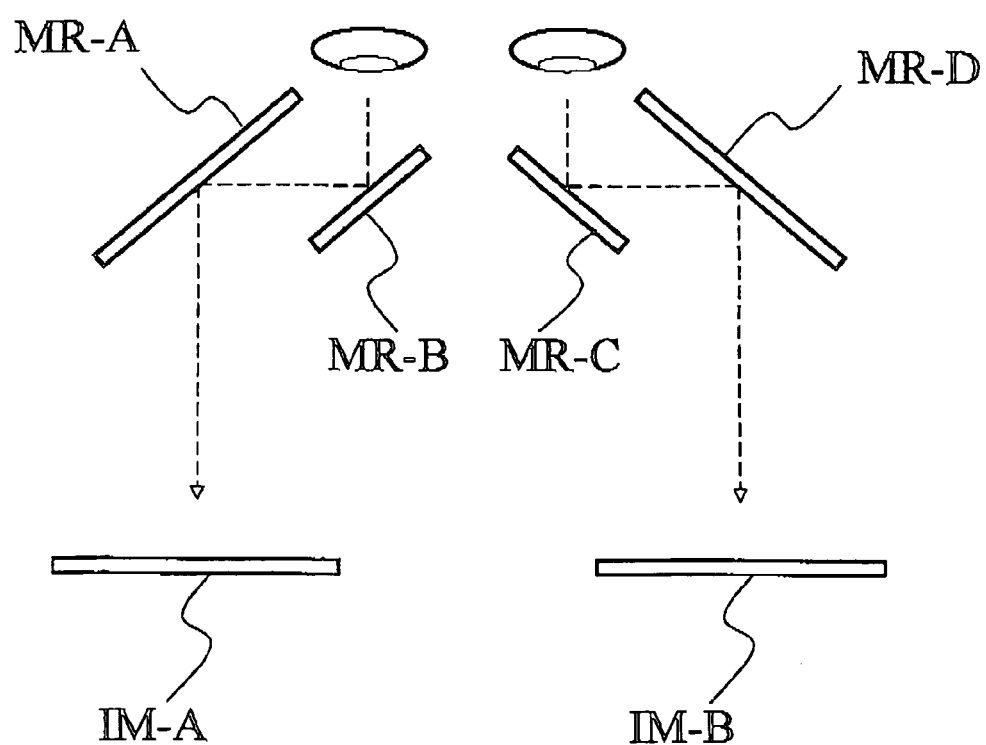
FIG. 11 is a typical view illustrating an example of detail method for composing a pair of stereoscopic TEM images.

FIG. 11 is a typical drawing illustrating an example of a detailed method for composing a pair of stereoscopic TEM images. Each of the TEM images, IM-A and IM-B, obtained by the stereoscopic observation is observed via the respective pair of reflecting mirrors, MR-A and MR-B, and MR-C and MR-D. When the right TEM image and the left TEM image are adequately moved to match the position of both images, a three-dimensional image is composed.

According to the embodiment of the invention, observation of an amorphous material is conducted by forming an image only by the transmission wave TW, which gives an advantage of allowing arbitrarily selecting the tilt angle in the arrow A direction and the arrow B direction in FIGS. 9A and 9B, respectively. That is, the stereoscopic observation by the transmission electron microscopy is normally conducted using the diffraction wave DW to obtain a pair of TEM images as the "stereo-pair" which reverses the sign of the reflection vector (g-vector). For example, the same lattice plane (such as a (111) reflection image and a (-1 -1 -1) reflection image) is adopted as the lattice plane inducing the diffraction.

To the contrary, according to the embodiment of the invention, the image is formed without using the diffraction wave DW so that such a type of limitation does not occur. Consequently, the tilt angle of the left specimen and the right specimen is arbitrarily determined, respectively, while taking into account of the distribution of defects DF, the surface condition of the specimen SP, and the thickness dispersion appearing during formation of the thin film specimen.

According to an experiment carried out by the inventors of the present invention, the tilt angle of the specimen is arbitrarily determined within a range from several degrees to several tens of degrees, as shown in FIGS. 9A and 9B. For example, a tilt angle of about 10 degrees has shown a tendency to form a favorable three-dimensional image.

As described above, according to the embodiment of the invention, the stereoscopic observation of defect in an amorphous material is conducted by forming image using only the transmission wave under an under-focus condition, thus clearly grasping the contrast of the defect while suppressing a the phase contrast originated from the microstructure of the amorphous material, and furthermore it becomes possible to grasp the three-dimensional shape and the distribution of the defect.

EXAMPLES

The embodiment of the invention will be described in more detail referring to the examples.

First Example

The TEM observation has been given to the respective materials for porous interlayer insulating films: a siloxane resin having the main structure of Si—O bond; a fluorine-laid silicon oxide (SiOF); and an organic polymer resin having an aromatic hydrocarbon structure.

The specimen for the TEM observation has been sliced to a wedge shape, and thinned to 200 nm or smaller thickness using focused ion beam (FIB). To prevent charge-up of the insulating film, the specimen may be coated by carbon (C) to thickness from several nanometers to several tens of nanometers. Nevertheless, an experiment conducted by the inventors of the present invention has shown that the insulating film which has been thinned to the above-described thickness range has not substantially shown deformation of the TEM image caused by the charge-up even without that kind of conductive coating, and that the observation has been conducted without problem.

When conducting the TEM observation, the size of an objective diaphragm allows only the transmission wave coming from the specimen to form the image. For the diffraction wave, the objective diaphragm has removed the diffraction waves equal to or higher than the first halo ring. In addition, the focus condition has been shifted from the Scherzer focus to under-focus side. Under those established conditions, a pair of stereo-photographs of the specimen has been taken at two different tilt angles.

Since a thus photographed observation image under the above-described conditions was formed using only the transmission wave, the phase contrast originated from the microstructure of the amorphous material is suppressed, and the contour of a pore and the density difference caused by the pore are emphasized. Furthermore, since the observation is conducted under the focus condition at further under-focus side than Scherzer focus, the sharpness of the phase contrast in the TEM image is lost, thus emphasizing the contour of a pore and the density difference caused by the pore.

In the strict sense, the transmission wave is made by successive dots. Since, however, the objective diaphragm has a finite aperture, complete rejection of the diffraction wave is difficult to attain. Accordingly, the contrast originated from the microstructure of the amorphous material cannot be completely removed (to Zero).

In this regard, further stereoscopic observation is given, and it is found that, since two observed images obtained from different specimen angles from each other are composed to form a single stereo-image, the contrast of microstructure which is left behind to some quantity in a dim state has no resolution of the stereo-structure in the depth direction of the specimen, and the contrast functions as the background of the observation image, so that the overlaying of the images give cancel of intensity, thus the pore becomes clearer.

Second Example

As the Second example of the embodiment of the invention, observation has been given on a composite material having an amorphous material and a crystalline material.

Figure 12:
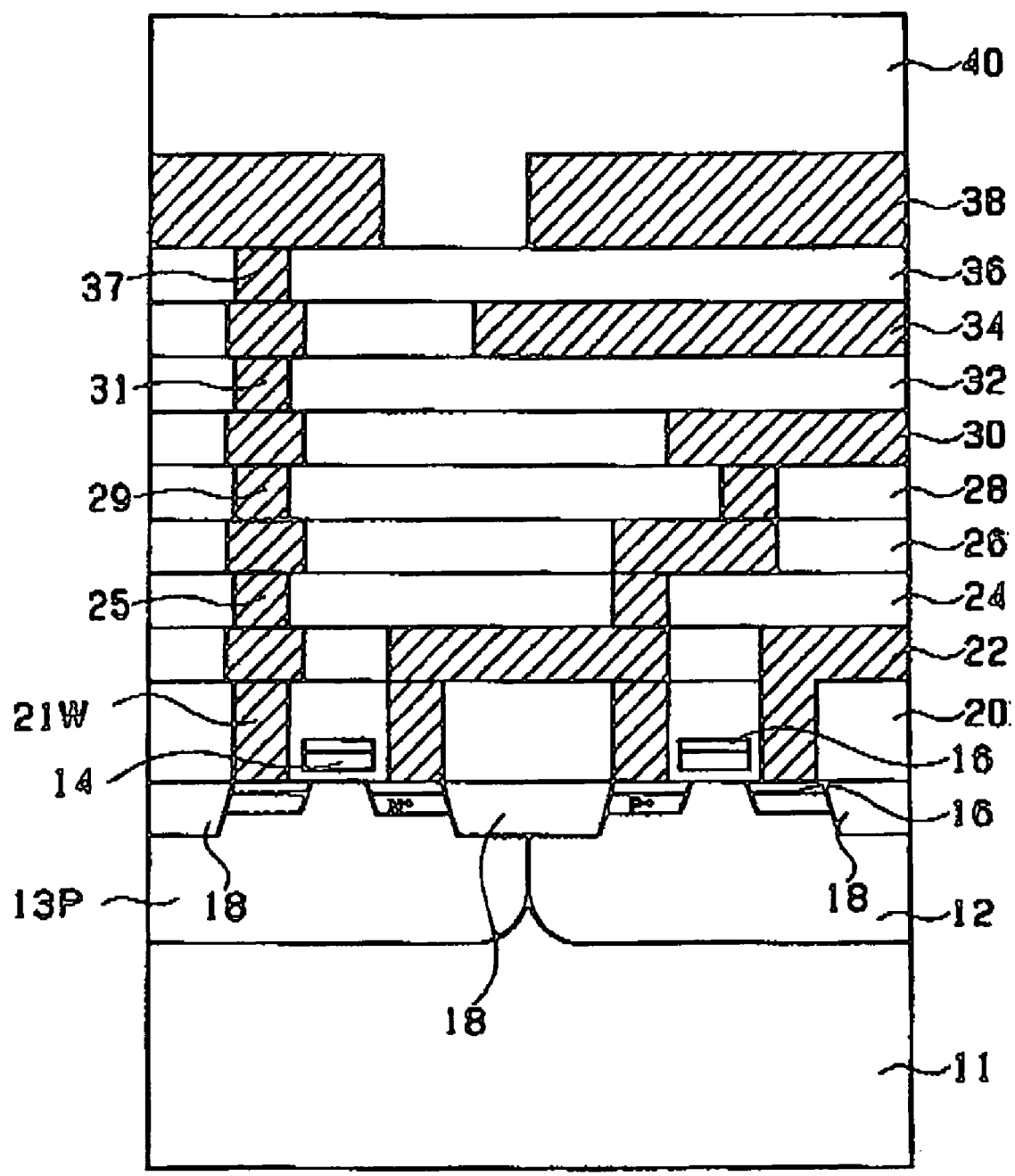
FIG. 12 is a typical view of the cross sectional structure of the semiconductor integrated circuit device observed in an example according to the embodiment of the invention.

FIG. 12 is a typical drawing of the cross sectional structure of a semiconductor integrated circuit device, observed in the Second example. The semiconductor device is a logic type device, and has a multilayer interconnection structure.

In the case of the semiconductor device, an N-well 12 and a P-well 13 are respectively formed on the surface of a silicon substrate 11, and a MOS transistor is formed on the respective surface layers thereof. The upper face of the transistor is covered with a first interlayer insulating film 20. Each of source, drain, and gate 14 of the transistor is provided with a silicide 15 as the electrode contact. The silicide 15 is connected with a first metallic interconnection layer 22 above thereof via a contact hole opened in the first interlayer insulating film 20 and via a buried plug made of tungsten (W).

A multilayer interconnection structure is formed above the first metallic interconnection layer 22. That is, a second interlayer insulating film 24 is located above the first metallic interconnection layer 22, and there are further located a second metallic interconnection layer 26, a third interlayer insulating film 28, a third metallic interconnection layer 30, a fourth interlayer insulating film 32, a fourth metallic interconnection layer 34, a fifth interlayer insulating film 36, and a fifth metallic interconnection layer 38 above the second interlayer insulating film 24, in this order. At above thereof, a passivation film 40 is positioned.

Each of these interlayer insulating films has via holes at an adequately pattern, and interconnections are vertically connected by the respective metallic buried plugs through the respective via holes.

Regarding the semiconductor device having the multi-layer interconnection structure, instead of aluminum (Al), which has been widely used until now as the metallic interconnection material, in order to suppress the CR delay in interconnection, copper (Cu), which has smaller resistivity and higher reliability than Al, is used.

On the other hand, to decrease the parasitic capacitance between interconnections, it is necessary to decrease the dielectric constant of $SiO_x$ which structures the interlayer insulating film, (low-k). To do this, pores are introduced to form the porous material.

In this regard, the inventors of the present invention have conducted TEM observations of the semiconductor device.

The specimen is prepared by slicing the semiconductor device in the vertical direction to the principal plane of the substrate 11 to form a wedge shape specimen, then by thinning the multilayer interconnection section to 200 nm or smaller thickness using FIB.

The TEM observation is given to the interlayer insulating film section, the metallic interconnection layer section, and the metallic buried plug section of via hole.

As for the interlayer insulating film section, the TEM observation is given under similar conditions with that applied in the First example. That is, the diffractive waves equal to or higher than the first halo ring are eliminated by the objective diaphragm, and a focus condition shifted from the Scherzer focus to under-focus side is established to take a pair of stereo-photographs of the specimen at two tilted angles thereof.

The result is similar with that of the first example, giving clear observation of three-dimensional shape and distribution of defect by suppressing the phase contrast originated from the microstructure of amorphous $SiO_x$, while emphasizing the contour of pore and the density difference by the pore.

Then, the observation condition is varied to observe the metallic interconnection layer section and the metallic buried plug section at via hole.

By widening the aperture of the objective diaphragm, an image is formed applying also higher diffraction waves. The specimen is tilted to take a pair of stereo-photographs from two different directions under the Scherzer focus condition or a focus condition near the Scherzer focus. As a result, three-dimensional shape at the metallic interconnection layer section and the metallic buried plug section at via hole is capable of being observed, respectively. Thus the stereo-shape thereof is accurately grasped. Furthermore, at near the center of the copper (Cu) of polycrystalline material in the buried section, a domain having high density of pores and defects is observed.

As described above, in the Second example, there is provided a TEM image showing clear defects therein on observing the semiconductor device having an-amorphous section and a crystalline section by adequately changing the observation condition for the respective sections.

The embodiment of the invention is described above referring to the examples. The present invention, however, is not limited to the examples.

For instance, the material of amorphous or crystalline material as the target of the observation method according to the embodiment of the invention is not limited to the above-described materials, and various other materials can be observed to give similar effect with that of the present invention.

The composite material which has an amorphous material and a crystalline material as the target of the observation method according to the present invention is not limited to the multilayer interconnection structure described above in the examples, and other various materials are applicable,. for example a micro-transistor and diode. In more detail, for example, a gate-insulating type micro-transistor, which is prepared by forming a gate insulating film as an amorphous material on a crystalline semiconductor layer then by providing a gate electrode made of polycrystalline silicon as the crystalline material on the gate insulating film, can be observed in three-dimensional mode.

Furthermore, all kinds of the method for observing defect by the transmission electron microscopy, which can be executed by the person skilled in the art through the modification of the design on the basis of the method for observing defect by the transmission electron microscopy described above as the embodiment of the invention are also within the scope of the present invention.

As described above in detail, according to the embodiment of the invention allows the observation of defect in an amorphous material to conduct clearly and surely, which observation had been difficult in the related art. Furthermore, the embodiment of the invention makes possible to grasp the three-dimensional shape and the distribution of defects, which significantly contributes to the industrial development.

While the present invention has been disclosed in terms of the embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A method for observing a defect in an amorphous material of a specimen by transmission electron microscopy, comprising:

generating an incident electron beam into the amorphous material;

eliminating generated diffraction waves equal to or higher than a first halo ring to form an image substantially only by a transmission wave coming through the amorphous material; and observing the image under an under-focus condition, wherein the observation is a three-dimensional observation of a defect by applying a plurality of observations with varied incident angles of the electron beam to the amorphous material, then by composing the results of the plurality of observations, and wherein the plurality of observations include a stereoscopic observation.

2. The method of observation by transmission electron microscopy according to claim 1, wherein the under-focus condition is a condition shifting from Scherzer focus condition to an under-focus condition.

3. The method of observation by transmission electron microscopy according to claim 1, wherein the amorphous material is an insulating film being contained in a semiconductor device, and the defect is a pore existing in the insulating film.

4. A method for respectively observing an amorphous material and a crystalline material in a composite specimen containing both of the amorphous material and the crystalline material by transmission electron microscopy, comprising:

when observing a defect in the amorphous material, injecting an electron beam into the amorphous material, eliminating generated diffraction waves equal to or higher than a first halo ring, and then forming an image substantially only by a transmission wave coming through the amorphous material to conduct observation thereof under an under-focus condition, while when observing the crystalline material, injecting the electron beam into the crystalline material, and forming an image by a generated diffraction wave and by a transmission wave coming through the crystalline material to conduct observation thereof, wherein the observation is a three-dimensional observation of a defect by applying a plurality of observations with varied incident angles of the electron beam to the amorphous material, then by composing the results of the plurality of observations, and wherein the plurality of observations include a stereoscopic observation.

5. The method according to claim 4, wherein the under focus condition is a condition shifting from Scherzer focus condition to an under-focus condition.

6. The method according to claim 4, wherein the amorphous material is an insulating film being contained in a semiconductor device, and the defect is a pore existing in the insulating film.

7. The method of observation by transmission electron microscopy according to claim 2, wherein a phase contrast originated from a microstructure of the amorphous material is weakened, and a contrast on a macroscopic defect is obtained relatively intensely by forming an image substantially by the transmission wave, and by making the under-focus condition shifted to a further under-focus condition from the Scherzer focus condition.

8. The method of observation by transmission electron microscopy according to claim 1, wherein the stereoscopic observation includes taking a pair of stereo-photographs of the specimen at two tilted angels thereof.

9. The method of observation by transmission electron microscopy according to claim 8, wherein the tilted angles are within plus or minus several degrees to several tens of degrees.

10. The method of observation by transmission electron microscopy according to claim 8, wherein the tilted angles are plus or minus about 10 degrees.

11. The method according to claim 5, wherein a phase contrast originated from a microstructure of the amorphous material is weakened, and a contrast on a macroscopic defect is obtained relatively intensely by forming an image substantially by the transmission wave, and by making the under-focus condition shifted to a further under-focus condition from the Scherzer focus condition.

12. The method according to claim 4, wherein the stereoscopic observation includes taking a pair of stereo-photographs of the specimen at two tilted angels thereof.

13. The method according to claim 12, wherein the tilted angles are within plus or minus several degrees to several tens of degrees.

14. The method according to claim 12, wherein the tilted angles are plus or minus about 10 degrees.

\* \* \* \* \*

UNITED STATES PATENT AND TRADEMARK OFFICE
CERTIFICATE OF CORRECTION

PATENT NO. : 7,083,992 B2 Page 1 of 1
APPLICATION NO. : 10/944842
DATED : August 1, 2006
INVENTOR(S) : Ogawa et al.

It is certified that error appears in the above-identified patent and that said Letters Patent is hereby corrected as shown below:

On the title page, Item (73), the Assignee information is incorrect. Item (73) should read:

-- (73) Assignees: Nissan Arc, Ltd., Yokosuka (JP);
Matsushita Electric Industrial Co., Ltd., Kadoma (JP) --

Signed and Sealed this

Nineteenth Day of February, 2008

JON W. DUDAS
*Director of the United States Patent and Trademark Office*